United States Patent [19]
Gross

[11] 4,064,228
[45] Dec. 20, 1977

[54] ANTIGENS AND IMMUNOASSAYS FOR MORPHINE AND RELATED 3-OXYBENZOMORPHAN COMPOUNDS

[75] Inventor: Stanley Joseph Gross, Encino, Calif.

[73] Assignee: Biological Developments, Inc., Encino, Calif.

[21] Appl. No.: 578,547

[22] Filed: May 19, 1975

Related U.S. Application Data

[60] Continuation-in-part of Ser. No. 528,044, Nov. 29, 1974, Ser. No. 462,517, April 19, 1974, Ser. No. 160,559, July 7, 1971, Pat. No. 3,940,475, and Ser. No. 480,097, June 17, 1974, abandoned, said Ser. No. 528,044, is a division of Ser. No. 253,632, May 15, 1972, abandoned, which is a continuation-in-part of Ser. No. 89,929, Nov. 16, 1970, abandoned, which is a continuation-in-part of Ser. No. 45,558, June 11, 1970, abandoned, said Ser. No. 462,517, is a continuation of Ser. No. 89,929, , said Ser. No. 160,559, is a continuation-in-part of Ser. No. 89,929, , said Ser. No. 480,097, is a continuation of Ser. No. 160,150, July 6, 1971, abandoned, which is a continuation-in-part of Ser. No. 89,929.

[51] Int. Cl.$^2$ .................... A61K 39/00; G01N 33/16; G21H 5/02

[52] U.S. Cl. .................................... 424/1; 23/230 B; 260/112 R; 424/12

[58] Field of Search ............................ 424/1, 1.5, 12; 23/230 B; 260/112 R

[56] References Cited

U.S. PATENT DOCUMENTS

| | | | |
|---|---|---|---|
| 3,709,868 | 1/1973 | Spector | 424/1 X |
| 3,822,245 | 7/1974 | Spector et al. | 424/85 X |
| 3,843,696 | 10/1974 | Wagner et al. | 424/12 X |
| 3,884,898 | 5/1975 | Schneider | 424/12 X |

OTHER PUBLICATIONS

Kabat, Structural Concepts in Immunology and Immunochemistry, Holt, Rinehart and Winston, Inc., New York, 1968, pp. 9–26.

Spector, Journal of Pharmacology and Experimental Therapeutics, vol. 178, No. 2, Aug., 1971, pp. 253–258.

Harwood, Pharmacology, vol. 11, 1974, pp. 52–57.

*Primary Examiner*—Benjamin R. Padgett
*Assistant Examiner*—Christine M. Nucker
*Attorney, Agent, or Firm*—McAulay, Fields, Fisher & Goldstein

[57] ABSTRACT

Antigens capable of generating antibodies specific to morphine and other 3-oxybenzomorphan compounds are prepared by conjugating 3-oxybenzomorphan derivatives with immunogenic carriers employing a linking site on an aryl group of the 3-oxybenzomorphan other than the hydroxyl substituent, so as to produce antibodies specific for the material.

26 Claims, No Drawings

ANTIGENS AND IMMUNOASSAYS FOR MORPHINE AND RELATED 3-OXYBENZOMORPHAN COMPOUNDS

CROSS-REFERENCE TO RELATED APPLICATIONS

This application is a continuation-in-part of my co-pending application Ser. No. 528,044, filed Nov. 29, 1974, which was a divisional of then co-pending application Ser. No. 253,632, filed May 15, 1972, abandoned which was a continuation-in-part of co-pending application Ser. No. 89,929, filed Nov. 16, 1970, now abandoned, which, in turn, was a continuation-in-part of my application Ser. No. 45,558, filed June 11, 1970, now abandoned; of my co-pending application Ser. No. 462,517, filed Apr. 19, 1974, which was a continuation of application Ser. No. 89,929, aforereferenced; of application Ser. No. 160,559, filed July 7, 1971, now U.S. Pat. No. 3,940,475, which was a continuation-in-part of application Ser. No. 89,929, aforereferenced; and of application Ser. No. 480,097, filed June 17, 1974, abandoned, which is a continuation of application Ser. No. 160,150, abandoned, filed July 6, 1971, which was a continuation-in-part of application Ser. No. 89,929, aforereferenced.

BACKGROUND OF THE INVENTION

1. Field of the Invention

This invention relates to a method for the preparation of antibodies which are specific for homologous hapten comprising a 3--oxybenzomorphan compound, for example, an opium alkaloid. The invention also relates to novel artificial or synthetic antigens useful for generating such specific antibodies. The antibodies produced in accordance with this invention are useful in immune assays of 3-oxybenzomorphans, in particular, morphine, heroin, codeine, and the metabolic derivatives thereof.

The immunologic terms employed herein are believed to be in accord with conventional usage and definition. Should any presently unforeseen confusion arise, unless otherwise indicated, the construction of a term shall be in accordance with its definition and usage in the well known textbook by Weiser, Myrvid and Pearsall, *Fundamentals of Immunology for Students of Medicine and Related Sciences*, published by Lea & Feiberger, Philadelphia, 1969.

2. Description of the Prior Art

A relatively new approach to biological assaying involves immunochemical procedures as a basis for the assay. Such procedures involve the use of antibodies which react with the compound to be assayed. A known amount of antibody and the sample, obtained from the test species, are intermixed. Theoretically, if the antibody is specific for the compound to be assayed (i.e., does not cross-react to a significant degree with biologically distinct structural homologs or analogs) one could then accurately measure the amount of antibody reacting with the test compound using conventional radioimmune or fluorescent competition assay techniques. This amount can then be translated into the amount of test compound present.

Heretofore, no immunochemical technique has been developed which produces a sufficiently reliable, reproducibly accurate opium alkaloid assay employing such immunochemical procedures. The problem, aside from the lack of sensitivity of available measurement techniques, has been that the antibodies produced in accordance with presently available methods are not sufficiently specific for the test compound. These prior art antibodies cross-react to an undersirable degree with the biologically distinct analogs or homologs of the test compound encountered in the serum sample under assay.

Antibodies to immunogenic compounds of high molecular weight, such as proteins, can be produced by administering the unaltered or natural compound to the antibody-producing host. However, small molecules which are not immunogenic by themselves, such as the opium alkaloids, must be bound to a high molecular weight immunogenic carrier. Such artificial antigens induce antibody formation. Substances which do not induce the formation of antibody, unless bound to a high molecular weight carrier, are herein termed "haptens" in conformance with conventional usage.

Conventionally, artificial antigens have been produced by conjugating immunogenic carrier molecules through the reactive functional groups on the haptenic molecule, e.g., see *J. Biol. Chem.*, 228:713 (1957); id., 234:1090 (1958); *Can. J. Biochem. Physiol.*, 36:1177 (1958); id., 39:941, 961 (1961); *Science*, 129:594 (1959); *J. Immun.*, 92:515 (1964); *Biochem.*, 9:331 (1970); *Science*, 168:1347 (1970); and *J. Pharmacol.*, 178:253 (1971). Such attempts to produce specific antibodies by coupling carrier molecules to one of the functional groups of the hapten have successfully rendered the hapten immunogenic. However, considerable cross-reactivity is demonstrated by biologically distinct structural analogs coupled at the same or similar sites. Such non-specific binding with related compounds nugates the specificity of these conventionally produced prior art antibodies. See *Steroids*, 16:387 (1970); id., 18:555, 593, 605 (1971); *Karolinska Symposia on Research Methods in Reproductive Endocrinology*, p. 320, Ed. E. Diczfalusky Bogtrykksiut Forum, Copenhagen (1970); and *Immunologic Methods in Steroid Determination*, Eds. Peron and Caldwell, Appleton-Century-Crofts, New York (1970), 41.

Another approach to the preparation of specific antibodies to small molecules involved coupling the immunogenic carrier into the aromatic ring of the hapten. For example, see Gross, *Immunochemistry*, 5:55 (1968), describing the synthesis of certain immunogenic steroid-protein conjugates and the production of rabbit antiserum to beta-estradiol, coupled to bovine serum albumin (BSA) and keyhole limpet hemocyanin (KLH). Antisera were tested for precipitation against steroids coupled to human gamma globulin (IgG). The immunological assays employed quantitative precipitin tests, but the all-important quantitative hapten inhibition tests were not performed. This reference does report evidence of antibodies but further reports that they cross-reacted substantially. Antibody to estradiol-KLH is reported to have brought down a non-specific precipitate with testosterone-IgG. The method used for synthesizing the conjugates comprised diazotizing para-aminobenzoic acid into the steroid and then coupling the carboxyphenylazosteroid to protein through the carboxyl group by carbodiimide condensation. The A-ring of an estrogen steroid is phenolic and, thus, azo coupling takes place adjacent the phenolic hydroxyl.

Most recently, an attempt to produce specific antibodies for 17-beta-estradiol by coupling bovine serum albumin via the alicyclic $C_6$ position was reported in *Steroids*, 18:605 (1971). The reported results do not support the claimed specificity. Also, Spector et al., *Science*, 179:1340 (1973), have reported the preparation of antibodies to serotonin; however, the reported results indicate substantially complete cross-reactivity with the closed related analog, methoxyserotonin (i.e., 5-methoxytryptamine).

In addition to the other shortcomings of the prior art, the materials taught are not 3-oxybenzomorphans and are quite distinct from these materials. The prior art neither teaches nor suggests methods of preparing antigens useful for producing 3-oxybenzomorphan antibodies.

To understand the importance of specificity to practical immunochemical competition assays one need only consider that a morphine assay must distinguish morphine from codeine, the commonly dispensed 3-methylmorphine, and, for that matter, from the important synthetic surrogates of morphine, such as, methadone, meperidine, and pentazocine.

Several attempts have been made to produce morphine antibodies with varying degrees of success. For example, such attempts have been reported in Hooker et al., *Journal of Immunology,* 38:479-490 (1940); Mingola et al., Atti. Acad. Italia, Rend. Classe Sci. Fis. Mat. Nat., (7), 2, 1103 (1941) [*Chemical Abstracts,* 39:1505, 1945]; Spector, U.S. Pat. No. 3,709,868, and the patent which resulted from a divisional application of that patent, U.S. Pat. No. 3,822,245; Leute et al., *J.A.M.A.,* 221:1231 (September 1972); and *Nature* (New Biology) 236:93–4 (1972).

Hooker prepared, or at any rate reported, morphine and strychnine azoproteins prepared by diazotizing aminomorphine and aminostrychnine into particular, individual proteins. In each case, the amino derivatives were prepared by nitration and then reduction of the parent alkaloid. There was no evidence of morphine-specific antibody. More success was obtained with strychnine and, apparently, antibody binding specifically with strychnine was obtained. Strychnine, however, does not come within the scope of the present invention, nor is it now of pharmaceutical interest. Although strychnine is an alkaloid, and has some structural features similar to opium alkaloids, it has important differences, notably, the fact that its aromatic ring is not hydroxylated.

Hooker's failure with morphine may be explained by the fact that his starting material was not, in fact, 2-aminomorphine, as was intended. It is known to the art that nitration of morphine probably does not yield any nitromorphine.

This failure of Hooker was recognized by Mingola, who refers to the Hooker work and who, accordingly, prepared a 2-azomorphine-coupled antigen employing a different route. Mingola diazotized acetyl-p-phenylene diamine, coupled the resulting material with morphine, removed the acetyl group so as to free the second amino group, and then diazotized that compound into serum. There is no showing of the production of antibody binding with morphine, and it is doubtful that Mingola can be said to disclose such antibody. His reports regarding antibody are generally qualitative and by no means clear as to final product. The most favorable interpretation of Mingola's results would appear to be that, for both morphine and strychnine, zonal precipitation reactions were obtained between the serum recovered from rabbits after administration of the above-described antigen and the separate products of diazotizing morphine and strychnine, respectively, with other sera, presumably, sera from a different species. Apparently, several other azo proteins did not produce such precipitation reactions. Mingola provides no data to support his qualitative statements and, most importantly, there are no hapten inhibition tests, such as were done by Hooker. These tests would have provided more definitive information on the character of Mingola's products. This paper is, thus, of little value to one working in this art and would not be used by one seeking the extreme assay sensitivities required.

According to the two Spector patents, an opium alkaloid antigen is prepared by derivatizing the 3-position hydroxyl to the corresponding carboxymethyl opium alkaloid, and then coupling that derivative to a proteinic carrier by carbodiimide condensation of the carboxyl with an available amine on the protein to form an amide bond. While this material has a number of advantages, it suffers from the disabling disadvantage of having a very high cross-reactivity with codeine. Spector, in the file of his U.S. Pat. No. 3,709,868, reports experiments conducted to reproduce the work of Mingola. While Spector employed bovine serum albumin, rather than Mingola's serum, a step which should have resulted in improved results, Spector reports the antibody raised to be of poor titer and high cross-reactivity.

Leute, in his two papers, is concerned with antigens similar to those of Spector for his antibodies and assays. Again, the antigens are 3-carboxymethyl opium alkaloids coupled to a protein through the carboxyl. Again, high cross-reactivity with codeine is reported.

Thus, all of the prior art known to applicant can be summarized with the statement that the only attempts to produce an opium alkaloid antibody that have been reported employed morphine, and the quantitative data reported show that the antibody raised has an extremely high cross-reactivity with codeine.

SUMMARY OF THE INVENTION

In accordance with the present invention, an antigen is provided for raising antibodies specific to a 3-oxybenzomorphan. This antigen has the formula:

$$[R-N=Y-R'-L]_nZ, \qquad (1)$$

including the stereo and geometric isomers. In the above formula, R is a 3-oxybenzomorphan compound; Y is selected from the class consisting of N and CH and is connected to a ring carbon atom of an aromatic component of R', R' also having a moiety capable of reacting with a functional group of Z; Z is a carrier molecule conferring immunogenicity, the combination of the moiety of R' and the functional group of Z forming the linking group L; and $n$ is from 1 to the number of available functional groups on Z in its unconjugated state. When Y is N, a diazo linkage is present, this diazo linkage being formed by diazotization of a primary amino group on the material from which R' is formed. When Y is CH, R' is the remaining aromatic component of an aromatic aldehyde, and CH is the condensation residue of the characteristic keto group of the aldehyde.

The carrier capable of conferring immunogenicity can be immunogenic itself. Under those circumstances, particularly if this carrier is protein, it should be a homogeneous one and having a generally narrow molecular weight range.

The antigen of formula (1) is of particular importance when prepared in a high state of purity, for example, at least 98% pure. To accomplish this, it may be necessary to purify the intermediates from which it is formed as, for example, by chromatographic purification, or high resolution fractional crystallization.

The 3-oxybenzomorphans, represented by R in formula (1), include opium alkaloids, such as morphine, codeine, and heroin, and 3-oxymorphinan compounds.

Thus, the present invention relates to a novel class of synthetic antigens comprising a 3-oxybenzomorphan hapten moiety linked to an immunogenicity-conferring carrier material through the available ring carbon atoms of the aromatic ring of the 3-oxybenzomorphan hapten moiety. As bonding is through an available ring carbon atom, all of the functional groups of the hapten which determine biological specificity, i.e., the antigen-determinant groups, are free and capable of asserting their native, determinant characteristics.

The availability of all determinant groups for assertion of their native, determinant characteristics distinguishes the novel, synthetic antigens of this invention from those described by the prior art for the production of antibodies to optium alkaloids and results in a heretofore unobtainable and highly unique degree of specificity on the part of antibodies produced by treating host animals with such antigens. These antibodies are readily isolated from body fluids obtained from host animals after treatment of these animals with the novel, synthetic antigens of this invention.

The antibodies of the present invention have a low cross-reactivity with closely related heterologous haptens. By heterologous haptens are meant substances which comprise a closely related structural analog of the native haptens employed according to the present invention. For example, heterologous haptens with respect to morphine are methadone, dextromethorpan, N-allylnormorphine, codeine, and monoacetylmorphine.

The term "native hapten" connotes a hapten which is unaltered structurally, chemically or biologically. The term "homologous hapten" connotes the hapten or antigen capable of binding specifically with an antibody population. For example, morphine is the homologous hapten for morphine specific antibody. Therefore, as used in this invention, "heterologous hapten or antigen" is a substance, other than a homologous hapten; usually a closely related structural analog of the homologous hapten or antigen.

The unique specifically of the antibodies of this invention is clearly demonstrated by results of fluorescence quenching of antibody utilizing a selected derivative of the homologous native hapten in competition with (1) native homologous hapten and (2) related native heterologous haptens as more fully described hereinafter. The native homologous hapten quantitatively inhibits the quenching phenomena whereas the heterologous haptens do not. Prior art antibodies, selected on the basis of their alleged specificity, fail to distinguish the homologous compound from its closely related analogs in increasing concentrations using standard inhibition tests.

As discussed previously, it is highly desirable to have an antibody population which can distinguish a homologous hapten or antigen from closely related molecules. Such antibodies are needed for use in immunochemical competition assays employing simple physical techniques and isotope assays to rapidly measure concentrations of small molecules in urine or serum. In addition to rendering such assays accurate and reliable, a sufficiently specific antibody can obviate the need for preliminary extraction of the sample. This has immediate applicability to radioimmune assays to significantly shorten the time presently required to carry out such assays. These antibodies are also useful in conducting immunochemical competition assays using quantitative fluorescence perturbation (i.e., inhibition of quenching, enhancement and polarization).

The primary aromatic amines preferably employed in formation of the group R' of formula (1) include those having at least one function other than the diazotizable amine capable of reacting with a functional group on the immunogenic carriers, Z, of the present invention. Such primary aromatic amines, when reacted in accordance with conventional diazotization techniques as, for example, are disclosed in K. H. Saunders, *The Aromatic Diazo Compounds and Their Technical Applications*, Edward Arnold & Co. (1949), for example pages 1–60, will produce a stable diazonium salt capable of coupling to the opium alkaloid haptens of this invention. Generally, such primary aromatic amines contain from about 6 to about 14 carbon atoms.

As examples of the carrier-reactive coupling substituents on R' there may be mentioned lower-alkylcarboxylic acids, primary or secondary lower-alkylamines, primary or secondary lower-alkylaminocarboxylic acids, lower-alkylisocyanates and the like. The carrier-reactive functional group to which resort may be had in a particular case is dependent upon the reactive groups available on the carrier Z available for coupling. Thus, when the reactive functional groups on Z available for selective coupling are, for example, amino or carboxyl, the substituents on R' can be tailored to couple with such groups, e.g., by providing an available carboxyl group for coupling to the amino function on Z, or alternatively, an available amino group to couple with the carboxyl function on Z. In both cases, an amide linkage is produced. Other coupling systems and the linkages resulting therefrom are detailed more fully in Table I of my aforesaid application Ser. No. 253,632.

The present invention is also directed to the use of the antibodies produced from the antigens of formula (1) in radioimmunoassays.

DETAILED DESCRIPTION OF THE INVENTION

The present invention is directed to antigens of the formula:

$$[R-N=Y-R'-L]_{n}Z, \qquad (1)$$

where R, R', Y, Z, and *n* are as previously defined. The haptenic materials employed in forming these antigens so as to produce the group R are the geometric, steric, and optical isomers, and their mixtures, of 3-oxybenzomorphan compounds having the formula:

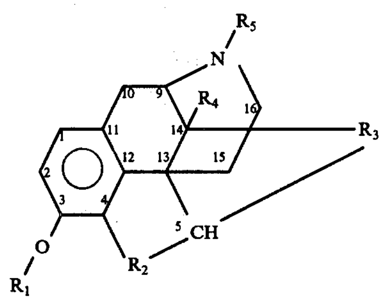

(2)

where $R_1$ is a member selected from the class consisting of hydrogen, ether-forming groups, and ester-forming groups; $R_2$ is a member selected from the class consisting of —0— and —H, H— ; $R_3$ is a member selected from the class consisting of ring-completing moieties of formula:

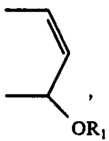 , 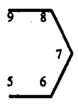 , 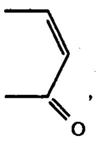 , 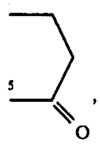 , and the 5-methyl substituents of such ring-completing moieties, and terminal moieties of formula —Q, Q'— where each Q and Q' are selected from the class consisting of hydrogen and lower alkyl radicals having from 1 to 6 carbon atoms; $R_4$ is a member selected from the class consisting of —H and —$OR_1$; and $R_5$ is at least one member selected from the class consisting of hydrogen, hydrocarbon groups having up to 20 carbon atoms and the nitrogen and oxygen derivatives thereof; and $R_3$ and $R_4$ can comprise the ring-completing moiety:

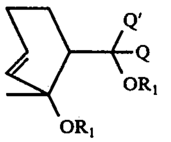

Ether-forming groups which are included within $R_1$ include lower hydrocarbon radicals of from 1 to 6 carbon atoms, either saturated or unsaturated. Particularly preferred ether-forming groups are methyl and ethyl. Other ether-forming groups represented by $R_1$ are organic moieties, with or without aromatic moieties, having up to 20 carbon atoms. They include both saturated and unsaturated radicals and those with nitrogen, sulfur, oxygen, phosphorus, or halogen members.

The ester-forming groups included within $R_1$ are any such conventional groups, including lower alkyl carbonyl radicals having from 1 to 7 carbon atoms, particularly acyl. Additionally, the ester-forming group can be nicotinate. As with the ether-forming groups, previously described, the ester-forming group can have up to 20 carbon atoms, with or without aromatic moieties, and the radical can include nitrogen, sulfur, oxygen, phosphorus, and halogen members.

Particularly preferred substituents with Q and Q' are hydrogen, methyl, ethyl, and cyclopropyl. Particularly preferred substituents within $R_5$ are hydrogen, methyl, ethyl, cyclopropyl, phenyl, phenylmethylene, and phenethyl. When $R_5$ includes two groups, as where the nitrogen is quaternized, the nitrogen atom will carry a positive charge.

Included within the above definitions of 3-oxybenzomorphans are two classes of compounds, the morphine derivatives in which $R_2$ is —O— and $R_3$ is a ring-completing group, and 3-oxymorphinans, in which $R_3$ is also a ring-completing group, but $R_2$ is —H, H—, so that there is no bridge atom between the No. 4 and No. 5 carbon atoms. In addition, the definition includes three-ring benzomorphan derivatives. For convenience, the numbering system in the various formulas given above is based upon morphine.

The morphine compounds of particular interest included within formula (1) are shown in Table 1. The 3-oxymorphinan compounds of formula (1) which are of particular interest are shown in Table 2. Other 3-oxybenzomorphan compounds of interest are shown in Table 3.

TABLE 1

| | $R_1$ | $R_2$ | $R_3$ | $R_4$ | $R_5$ |
|---|---|---|---|---|---|
| morphine | H | —O— | 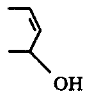 | H | $CH_3$ |
| codeine | $CH_3$ | —O— | 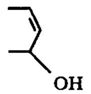 | H | $CH_3$ |
| heroin | $CH_3.CO$ | —O— | 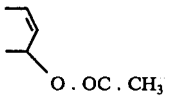 | H | $CH_3$ |
| monoacetyl morphine | $CH_3.CO$ | —O— | 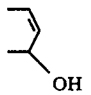 | H | $CH_3$ |
| dihydrodesoxymorphine-D | H | —O— | 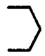 | H | $CH_3$ |
| 5-methyldihydromorphinone | H | —O— | 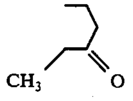 | H | $CH_3$ |
| 14-cinnamyloxycodeinone | $CH_3$ | —O— | 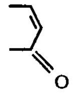 | 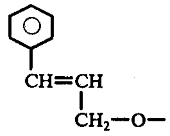 | $CH_3$ |

TABLE 1-continued

| | $R_1$ | $R_2$ | $R_3$ | $R_4$ | $R_5$ |
|---|---|---|---|---|---|
| unnamed | $COCH_3$ | —O— | 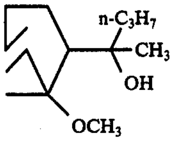 | | $CH_3$ |

TABLE 2

| | $R_1$ | $R_2$ | $R_3$ | $R_4$ | $R_5$ |
|---|---|---|---|---|---|
| 3-methoxy N-methyl morphinan (the d-form is dextromethorphan) (the 1-form is levorphanol) | $CH_3$ | —H, H— | 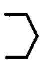 | H | $CH_3$ |
| N-cyclopropylmethyl morphinan (cyclorphan) | H | —H, H— | 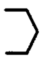 | H | 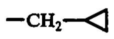 |
| N-β-furylethyl levorphanol | $CH_3$ | —H, H— | 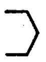 | H | 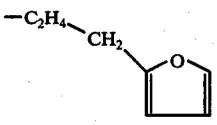 |
| N-p-aminophenethyl levorphanol | $CH_3$ | —H, H— | 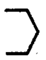 | H | 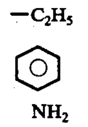 |
| levophenacylmorphan | $CH_3$ | —H, H— | 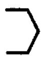 | | 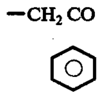 |

TABLE 3

| | $R_1$ | $R_2$ | $R_3$ | $R_4$ | $R_5$ |
|---|---|---|---|---|---|
| N-phenethyl 3-methyl benzomorphan | H | —H, H— | —H, $CH_3$ | H | $C_6H_5C_2H_4$— |
| pentazocine | H | —H, H— | —H, $CH_3$ | H | $CH_2CH{=}C(CH_3)_2$— |
| cyclazocine | H | —H, H— | —H, $CH_3$ | H | 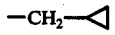 |

In general, the compounds illustrated in Tables 1, 2, and 3, and defined by formula (1), are either powerful analgesics, or antagonists to those analgesics. Many of the compounds are addictive, or create drug dependence. In part, the definitions of the 3-oxybenzomorphans, and their properties, are based upon *Textbook of Organic Medicinal and Pharmaceutical Chemistry,* Wilson et al, 6th ed., J. B. Lippincott Co. Philadelphia (1971), pp. 699–714, and that portion of the referenced text is herein incorporated by reference.

The novel synthetic antigens, depicted by the formula set forth herein, can be prepared in accordance with several preparative techniques. Generally these involve coupling a diazotized moiety, for example, diazotized p-aminobenzoic acid (or its methyl ester) to the 3-oxybenzomorphan haptenic moiety of this invention. The resulting azo derivative is then coupled to the immunogenic carrier, Z, the azo derivative being first converted to the free acid if necessary. Where the functional group on the azo derivative available for reaction with the functional group of the immunogenic carrier is an amino or carboxyl group, coupling to the available carboxyl or amino group of the immunogenic carrier, particularly in those cases where the carrier is a protein, can be effected using conventional carbodiimide condensation techniques.

Preferred synthetic antigens of formula (1) may be prepared according to the following reaction sequence:

Reaction Sequence I

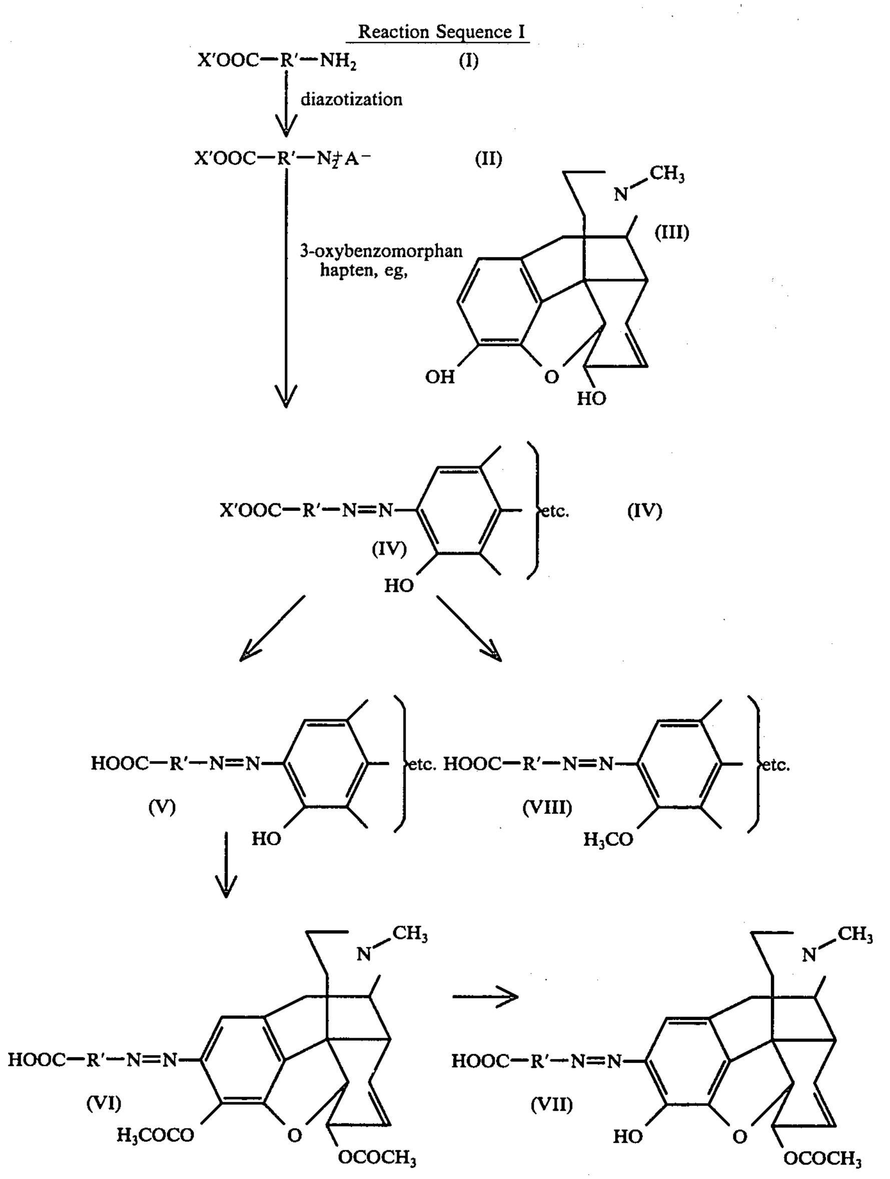

In the reaction sequence, R' is as previously defined, X' is a member selected from the class consisting of hydrogen and lower acyl radicals, particularly those having from 1 to 4 carbon atoms, and A is the anionic residue of a diazonium salt, generally the conjugate base of a strong mineral acid.

Referring to Reaction Sequence I, the 3-oxybenzomorphan azo derivative IV is novel and forms an embodiment of this invention. It is prepared from the 3-oxybenzomorphan (III), containing a phenolic hydroxyl in the 3 position on the aromatic ring, by reaction with the diazonium salt (II), which latter is derived from compound I under conventional diazotizing conditions. Generally an excess of nitrous acid is employed, preferably from about 0.75 equivalent to about 1 equivalent of the compound I, employed in the presence of about 0.85 to about 1.2 equivalents of nitrous acid. The diazotization is carried out in a strong mineral acid solution. The nitrous acid is usually generated by the addition of a solution of sodium nitrite to the mixture of the compound I in the excess mineral acid. Generally the reaction is maintained at a temperature of below 5° C., preferably 0° C. The resulting diazotized compound (II) is added to approximately an equivalent concentration (e.g., 1–1.35 equivalents) of the opium alkaloid (III), resulting in formation of the azo derivative (IV). The 3-oxybenzomorphan is generally maintained in a buffered solution having a pH of about 11. Acidification with mineral acid, preferably HCl, occasions precipitation of the desired azo opium alkaloid derivative (IV) in crude form.

Purification of the azo morphine alkaloid is carried out using chromatographic techniques. Silica gel column chromatography provides azomorphine alkaloid in substantially pure form, i.e., greater than about 98% by weight pure. Where X' is alkyl, hydrolysis of IV in basic solution gives the carboxyl derivative of the azo morphine alkaloid V. This may be acetylated conventionally, e.g., by room temperature reaction with acetic anhydride, to give the diacetyl azomorphine alkaloid (VI). Selective hydrolysis of VI provides the monoacetylazomorphine alkaloid (VII). Selective methylation of IV, followed by hydrolysis (where X' is alkyl), affords the 3-methoxyazomorphine alkaloid (VIII).

Similarly, where the target hapten contains ether or ester groups, it may be desirable to form them, or re-form them, after diazotization.

In order to be capable of conferring antigenicity, the carrier will normally be antigenic itself, although it may be an incomplete antigen, becoming complete only when coupled to the hapten. To be antigenic, the carrier must be an immunogenic substance, that term being used to refer to a substance capable of eliciting production of antibodies in a host animal to which the immunogenic substance is administered. While, in general, it is believed that the terms "carrier" and "immunogenic substances" are clearly understood in the art, and the discussion herein is not meant to modify the ordinary significance of the terms, further definition is provided here for a clearer understanding of the development.

The animal to which the antigenic substance is administered must be one having an effective immunological system. The immunogenic substances must be "foreign" to the animal, in the sense of not being "self." That is, the immunogenic substance administered must not be one which is a natural body substance of the animal and would, therefore, be accordingly tolerated by the animal's immunological system.

Generally, the antibodies elicited upon injection of the immunogenic substance into the animal will be generated by the host animal and will be capable of reacting or binding with the antigen in an observable and selective way. Thus, the antibodies will display some degree of discrimination between the administered immunogenic substance and other immunogenic materials.

The requirements for immunogenicity are not fully understood. However, it appears that for a molecule to be antigenic, it must have a certain complexity and a certain minimal molecular weight. Formerly, it was thought that the lower molecular weight limit to confer antigenicity was about 5,000. However, antigenicity has recently been demonstrated with molecules having molecular weights as low as 2,000. Molecular weights of 3,000 and more appear to be more realistic as a lower limit for immunogenicity, and approximately 6,000 or more is preferred.

Exemplary immunogenic carrier materials are those set forth in Cremer et al. "Methods in Immunology," (1963), W. A. Benjamin Inc., New York, pages 65 to 113. That disclosure is herein incorporated by reference. The carrier material can be a natural or synthetic substance, provided that it is an antigen or a partial antigen. For example, the carrier material can be a protein, a glycoprotein, a nucleoprotein, a polypeptide, a polysaccharide, a lipopolysaccharide, or a polyaminoacid. An example of an apparently incomplete antigen is the polypeptide, glucagon.

A preferred class of natural carrier materials is the proteins. Proteins can be expected to have a molecular weight in excess of 5,000, commonly in the range of from 34,000 to 5,000,000. Specific examples of such natural proteins are bovine serum albumin (BSA), keyhole limpet hemocyanin (KLH), human immunogammaglobulin (HGG), and thyroglobulin.

Exemplary of the synthetic carrier as a polyaminoacid, polylysine. Where the synthetic antigen comprises a partially antigenic carrier conjugated with a hapten, it will generally be desirable for the conjugate to have a molecular weight in excess of 6,000, although somewhat lower molecular weights may be useful.

Preferably, the natural carrier has some solubility in water or aqueous alcohol. Also preferably, the synthetic antigen is water soluble. Desirably, the carriers are non-toxic to the animals to be used for generating antibodies.

The carrier must have a, or preferably a plurality of, functional moieties by means of which it can be coupled. Of course, these groups can be introduced synthetically. Preferably, in practicing the present invention, a single carrier moiety should have a plurality of hapten moieties coupled to it, for example, from about 10 to about 70. In general, the maximum possible number of haptenic moieties per carrier molecule is preferred. Subject to steric hindrance, the maximum number will be determined by the number of reactive coupling groups on the carrier. For example, with BSA, it appears that the maximum number of haptenic moieties that can be coupled is between 60 and 70.

The assay, according to the present invention, is an immunochemical method of assaying for the presence of a target according to the present invention, that target being contained in a sample. The method employs an antibody obtained by the immunologic response of a vertebrate aminal to administration of an antigen according to the present invention, and the antibody is specific to the target. Further, the assay employs a standard, the standard and target competitively binding with the antibody to form an antibody-standard complex and an antibody-target complex. The antibody-standard complex has an artificially introduced radiation label so that the complex can be assayed quantitatively by measurement of the radiation emanating from it. In order for the method to be properly employed, the affinities of the antibody for the standard and for the target must be known quantitatively. In employing the method, a known quantity of the sample and a known quantity of the standard are allowed to compete for binding with a known quantity of the antibody. The radiation emanating from the antibody-standard complex so formed is determined so that the quantity of antibody-bound standard can be calculated and the quantity of target in the sample can be deduced. This deduction is carried out by attributing any difference between the quantity of bound standard determined and the quantity expected, based on the known binding characteristics of the antibody, to binding of the antibody with the target.

In an embodiment of the assaying procedure, the introduced label is radioactive and the antibody-standard is separated from any non-complexed, labeled material after allowing competition binding and before determination of the radiation emanated.

In another embodiment of the assaying method, the introduced label is fluorescent and the standard is provided with a chemical moiety giving it a fluorescence spectrum overlapping the natural fluorescence spectrum of the antibody. The complex can then be assayed by measurement of the perturbation of the antibody fluorescence due to binding with the standard.

The standard is a substance known to bind with the antibody and can be, for example, the target, the antigen used to raise the antibody, or the hapten used to make the antigen. Similarly, it can be a similar antigen having the same hapten bound to a different carrier, but at the same position on the hapten. Conveniently, where the radiation constitutes radioactive emission, such as beta or gamma rays, the standard can carry the radioactive label in the form of a radioactive isotope, e.g., tritium, $I^{125}$, or $C^{14}$, although, as an alternative, the antibody can be labeled.

When separation of the complex from the unreacted standard is necessary, as is normally the case with radioactive labeling, this can be effected by phase separation, insolubilizing of one of the components to be separated, etc. Thus, with a labeled antibody, the use of an antigenic standard having a plurality of antibody binding sites causes the antibody-standard complex to precipitate while, if the target is a small molecule, the antibody-target complex will remain in solution. Alternatively, the antibody can be insolubilized, as described elsewhere in the specification, and the standard labeled, so that unreacted standard stays in solution and can easily be separated from the complex.

One example of such a separation is the addition of saturated ammonium sulfate to the complexed mixture. The mixture, with the added ammonium sulfate, is then centrifuged which results in deposition of most of the protein, including the antibody-standard complex. The antibody-standard complex can then be removed as a solid and measurement carried out on this solid. Alternatively, the uncomplexed liquid standard is subjected to measurement or radiation emanation.

A further possibility is to absorb the standard with dextran-charcoal, after allowing for competition binding, and to then make the scintillation count for radiation on the liquid phase containing the antibody-standard complex following separation of the solid phase which contains the unreacted standard. In this case, the standard is labeled and is a small molecule, especially a radioactive isotope labeled target molecule.

While the count for radiation is normally made upon the antibody-standard complex, as this is either more convenient or is believed to reduce experimental error, it will be clear that where there is a separation of unbound, labeled material from the antibody-standard complex, the determination of the radiation emanating from the antibody-standard complex can equally well be made by measuring the radiation emanating from the unreacted, labeled material. From this measurement, the difference from the known amount of labeled material added can be calculated.

The term "radiation" is used in an ordinary dictionary sense and refers to energetic emissions originating from individual atoms or molecules which are generally attributed to internal changes within the atom or molecule. These emissions are in contrast to physical phenomena, such as, for example, precipitations which are the result of the inter-molecular or inter-atomic effects, and may require a large-scale cooperation of a great number of atoms or molecules to be meaningfully expressed. Radiation is significant for immunoassays as it provides a means of remotely monitoring the behavior of very small quantities of matter.

Thus, in addition to energetic emissions, radiation includes such phenomena as fluorescence and electron spin resonance. Fluorescence usually requires excitation by exposure to ultraviolet light, but the product is radiation. Thus, energy, usually in the form of light, is emitted as a result of intra-molecular change.

Where fluorescence is the form of radiation measured, it is feasible for the assay to be conducted without any separation of materials. Thus, antibodies, which are naturally fluorescent, have an absorption spectrum and an emission spectrum. If the standard chosen is a molecule having, as a label, a chemical group which fluoresces in spectra overlapping the antibody, then, when the standard complexes with the antibody, the natural fluorescence of the antibody is perturbed by that of the standard, and this perturbation can be measured. When the emission spectrum of the standard overlaps the absorption spectrum of the antibody, fluorescence enhancement will be observed from the complex at the antibody emission wavelength, and when the absorption spectrum of the standard overlaps the emission spectrum of the antibody, fluorescence quenching will be observed from the complex at the antibody emission wavelength. Comparable effects can be displayed using polarization perturbation.

Electron spin resonance labeled assays can also be conducted without the need for separation. A paramagnetic labeling group, such as a nitroxide ring, is attached, for example, to the standard. When subjected to a microwave frequency magnetic field, an electron spin resonance spectrometer can detect distinct resonance peaks characteristic of the nitroxide ring label. When the standard combines with antibody, these peaks are substantially extinguished, providing a direct indication of the degree of binding.

In order that those skilled in the art may be better enabled to practice the teachings of the present invention, the following examples are given by way of illustration, and not by way of limitation.

EXAMPLE 1

2-(4'-carboxyphenylazo) morphine

A. 4-Carboxyphenyldiazonium Chloride Ethyl Ester

A mixture of 1.91 g. (0.0115 mol) of ethyl p-aminobenzoate and 8.2cc of 6N hydrochloric acid was cooled in an ice water bath. A cooled solution containing 1.175g (0.0170 mol) of sodium nitrite in 3 cc of water was added dropwise to the amine hydrochloride until the solution gave an acid with moist potassium iodide starch paper.

B. 2-(4'-carboxyphenylazo) morphine ethyl ester

The pH of a solution containing 3.50 g (0.0115 mol) morphine sulfate monohydrate dissolved in 15 cc of 1 N sodium hydroxide was adjusted to pH 9–11 with dilute hydrochloric acid, and the resulting solution was then cooled to between 0°–5° C in an ice water bath. The cold 4-carboxyphenyldiazonium chloride ethyl ester was added dropwise while maintaining the pH and temperature of the reaction at 9–10 and 0°–5° C, respectively. After the addition of the diazonium salt was complete, the reaction was stirred for 2 hours at 0°–5° C and 1 hour at room temperature. The pH was then adjusted to 5 with dilute hydrochloric acid and the solvent removed under vacuum. The solid residue was extracted with 3×30 c.c. of anhydrous butanol. The extracts were combined and evaporated and the residue was purified on a silica gel column eluted with benzene-methanol-ammonium hydroxide (60:40:1).

C. 2-(4'carboxyphenylazo) morphine monohydrate

Treatment of 1.0g (0.002 mol) 2-(4'-carboxyphenylazo) morphine ethyl ester with 50 cc of 0.5–1.0N sodium hydroxide for 24 hours at room temperature and then adjusting the pH to 5 with dilute hydrochloric acid and filtering the precipitated solid gave a quantitative yield of 2-(4'carboxyphenylazo) morphine monohydrate. After recrystallization twice from 50% ethanol a red-brown solid was obtained which did not melt up to 315° C. Elemental analysis showed C, 64.39; H, 5.33; N, 9.28 percent. Calculated values for 2-(4'carboxyphenylazo) morphine ($C_{24}H_{25}O_6N_3$) are C, 63.84; H, 5.58; N, 9.31 percent. The nuclear magnetic resonance spectrum of the product was consistent with the structure of 2-(4'carboxyphenylazo) morphine. The mass spectrum of 2-(4'-carboxyphenylazo) morphine was obtained using a Picker Nuclear MS-9 mass spectrometer at an inlet temperature of 205° C. It showed a parent peak of 433 m/e, corresponding to the molecular weight of 2-(4'carboxyphenylazo) morphine. The fragmentation pattern could be rationalized.

EXAMPLE 2

2-(4'carboxyphenylazo) -3, 6-diacetylmorphine

A mixture of 1.0g (0.0019 mol) 2-(4'carboxyphenylazo) morphine, 20cc acetic anhydride and 20cc of anhydrous pyridine was heated at between 70°-80° C. for 24 hours. The reaction mixture was then cooled to room temperature and evaporated to dryness under reduced pressure. The resulting solid product was recrystallized twice from aqueous ethanol and dried. Thin layer chromatography using the solvent system benzene-methanol-ammonium hydroxide (60:40:0.5) showed only one spot. The nuclear magnetic resonance spectrum was consistent with the assigned product.

EXAMPLE 3

2-(4'carboxyphenylazo) -6-monoacetylmorphine

A solution of 0.5g of 2-(4'carboxyphenylazo)-3,6-diacetylmorphine in 10 ml 0.1 N NaOH was stirred at room temperature and examined hourly by silica gel TLC for the presence of the monoacetyl derivative, the solvent system being methylene chloride: methanol: water: acetic acid (80:20:1:1) and the rf value for azomonoacetyl morphine 0.39. When TLC showed most of the starting material to have hydrolyzed the reaction mixture was concentrated and passed down a silica gel column. The fraction containing the desired product was evaporated to dryness to give 2-(4'carboxyphenylazo) -6 acetyl morphine.

EXAMPLE 4

2-(4'-carboxyphenylazo) codeine

A. 4-carboxyphenyldiazonium chloride ethyl ester

A mixture of 1.66 g (0.01 mol) of ethyl p-aminobenzoate and 5 cc of 6N hydrochloric acid was cooled in an ice water bath. A cooled solution containing 1.03g (0.015 mol) of sodium nitrile in 3 cc of water was added dropwise to the amine hydrochloride until the solution gave an immediate positive test for excess nitrous acid with moist potassium iodide-starch paper.

B. 2-(4'-carboxyphenylazo) morphine ethyl ester

The pH of a solution containing 3.03 g (0.01 mol) morphine hydrate dissolved in 15 cc of 1 N sodium hydroxide was adjusted to 9 with dilute hydrochloric acid, and the resulting solution was then cooled to between 0°-5° C in an ice water bath. The cold diazonium salt, 4-carboxyphenyldiazonium chloride ethyl ester, was added dropwise while maintaining the pH and temperature of the reaction at 8.5-9.5 and 0°-5° C, respectively. After the addition of the diazonium salt was complete, the reaction was stirred for 1 hour at 0° C and 1 hour at room temperature. The pH was then adjusted to 5 with dilute hydrochloric acid and the solvent removed under vacuum. The solid residue was extracted with 3×30 cc of anhydrous butanol. The extracts were combined and evaporated and the residue was purified on a silica gel column eluted with benzene-methanol-ammonium hydroxide (60:40:1).

The methohydroxide of dimethyl aniline was prepared by adding 5.5g of the methyl benzene sulfonate of dimethyl aniline to an ethanolic solution of sodium ethoxide (0.45 g sodium in 4.5 ml ethanol) and removal of the sodium benzene sulfonate by filtration.

To this ethanolic solution of the methohydroxide was added 6.8 gm of (2) and the reaction mixture heated on an oil bath until all the ethanol was expelled and the temperature of the reaction mixture had risen to 110°, at which temperature it was maintained for 1 hour. The mixture was acidified with 15% acetic acid and the dimethyl aniline removed by steam distillation. The 2-(4'-carboxyphenylazo) codeine was then liberated from its acetate by addition of 2N sodium hydroxide solution (50 ml) followed by stirring for 24 hours. The pH was then adjusted to 5 with hydrochloric acid and the precipitated 2-(4'-carboxyphenylazo) codeine collected.

The foregoing examples demonstrate the preparation of the azo intermediates of preferred opium alkaloids. These azo intermediates within the scope of the invention are coupled to protein using conventional carbodiimide coupling techniques. Temperatures are not critical and generally range from about −10° C to about 25° C. The reaction is carried out in aqueous solution at a pH of 3.9 to 4.1 preferably. It is preferred to react the azomorphine alkaloid and carbodiimide in the presence of the protein to be conjugated (eg, keyhole limpet hemocyanin, bovine serum albumin, immunoglobulin G, thyroglobulin, etc.). Generally the protein is added to a mixture of other ingredients. Protein conjugation occurred at temperatures ranging from about −10° C to about 25° C, but can range as high as 60° C. Aqueous reaction mixtures are employed.

To couple the azomorphine alkaloids to the desired protein other coupling techniques can be employed (e.g., Kabat, Supra, page 20). Alternatively the carboxyazomorphine alkaloids may be coupled to proteins using isobutylchlorocarbonates as described, for example, in example 23 of my aforesaid application Ser. No. 253,632. The reaction sequence I is further demonstrated by the following specific examples.

On completion of the coupling reaction the unreacted opium alkaloid hapten molecules, coupling agent, and any reaction by-products are removed by dialysis or by passage down a suitable Sephadex column. The dialysis may be carried out using either distilled water or aqueous basic solution followed by dialysis against buffer of a given pH. When chromatographic separation is used, the eluant may be checked for presence of the pure protein fraction. A solution of purified antigen is recovered in each case. This may then be lyophilized.

Although in the foregoing reaction sequence I hapten: protein ratios are represented in terms of one mole of hapten per mole of protein, it should be recognized that these ratios will vary over a fairly wide range depending upon the ratio of hapten to protein employed in the coupling step.

Generally, excellent synthetic antigens having demonstrated antigenicity in host animals have been achieved using approximately a 25 molar excess of hapten to protein, the proteins of choice being keyholelimpet hemocyanin, bovine serum albumin, and immunoglobulin G. The resulting conjugated or coupled opium alkaloid hapten-protein (or other immunogenic carrier material as defined herein), produced in accordance with the invention generally have a hapten to protein ratio ranging from about 5:1, preferably from about 15:1, up to about 30 to 35:1 moles of hapten per mole of protein. Other proportions of hapten protein can obviously be employed and these can range as high as solubility permits but generally should not exceed, for practical reasons, 1,000:1, assuming solubility at this range.

The following Examples illustrate the coupling of these azo derivatives to immunogenic carriers to produce novel synthetic antigens within the scope of the invention.

EXAMPLE 5

2-(4'-carboxyphenylazo) morphine-bovine serum albumin

To a solution of 500 mg bovine serum albumin (BSA) in 20 ml distilled water was added a solution of 75 mg 2-(4'-carboxyphenylazo) morphine dissolved in 5 ml 0.01 M NaOH and the pH of the resulting solution was adjusted to 3.9 to 4.1 with 1 N HCL. To this solution was added 80 mg of 1-cyclohexyl-3-(2-morpholinoethyl) carbodiimide metho-p-toluene sulfonate and the reaction mixture stirred for 12 hours at 4° C while monitoring the pH. The pH was adjusted to 7.0 and the solution dialyzed against 6 liters of 0.15 M sodium carbonate at 4° C for 1 week with daily changes of the sodium carbonate solution. It was next dialyzed against 6 liters of 0.1 M sodium phosphate buffer (pH 7.4) at 4° C for 2 days with daily changes of the phosphate buffer solution. The protein concentration was determined by measurement of optical density and adjusted to give a 1% solution by the addition of distilled water.

EXAMPLE 6

2-(4'-carboxyphenylazo) morphine-keyholelimpet hemocyanin (KLH)

Example 5 was repeated, with the exception that 500 mg keyholelimpet hemocyanin was employed instead of bovine serum albumin. The protein concentration of the end-product, 2-(4'-carboxyphenylazo) morphine-KLH was determined by measurement of optical density and adjusted to a 1% solution by the addition of distilled water.

EXAMPLE 7

2-(4'-carboxyphenylazo) codeine-bovine serum albumin (BSA)

The process of Example 5 was repeated with the exception that 75 mg of 2-(4'-carboxyphenylazo) codeine was employed instead of the corresponding morphine derivative to yield the corresponding codeine-BSA synthetic antigen. The protein concentration was determined by measurement of optical density and adjusted to a 1% solution by the adding of distilled water.

EXAMPLE 8

2-(4'-carboxyphenylazo) codeine-keyholelimpet hemocyanin

The process of Example 5 was repeated with the exception that 500 mg of keyholelimpet hemocyanin (KLH) was employed instead of BSA to yield the desired 2-(4'-carboxyphenylazo) codeine-KLH. The protein concentration was determined by measurement of optical density and adjusted to a 1% solution by the addition of distilled water.

EXAMPLE 9

2-(4'-carboxyphenylazo) diacetyl morphine - BSA

The process of Example 5 is employed with the exception that 75 mg 2-(4'-carboxyphenylazo) diacetyl morphine are employed in place of the morphine derivative of Example 5. Also the dialysis procedure set forth in Example 5 is not employed, the product produced at the end of the carbodiimide condensation being employed without further purification after being diluted to a 1% protein solution by addition of distilled water (after measurement of optical density).

EXAMPLE 10

2-(4'-carboxyphenylazo) diacetyl morphine-keyholelimpet hemocyanin

The process of Example 5 is employed with the exception that 75 mg 2-(4'-carboxyphenylazo) diacetyl morphine are employed in place of the morphine derivative of Example 5. Also the dialysis procedure set forth in Example 5 is not employed, the product produced at the end of the carbodiimide condensation being employed without further purification after being diluted to a 1% protein solution by addition of distilled water (after measurement of optical density).

EXAMPLE 11

2-(4'-carboxyphenylazo) diacetyl morphine Polylysine

A solution of 100 mg hydrobromide salt of polylysine (MW 3000–30,000) was dissolved in 5 ml distilled water and the pH adjusted to 10–11. To this solution was added 50 mg 2-(4'-carboxyphenylazo) diacetyl morphine and the solution stirred to dissolve it. The pH was adjusted to 3.9–4.1; 60 mg cyclohexyl-3-(2-morpholinoethyl) carbodiimide metho-p-toluene sulfonate was added to the mixture and it was then stirred for 6 hours. The reaction mixture was shaken with several 5 ml portions of ether to remove free 2-(4'-carboxyphenylazo) diacetyl morphine and the aqueous fraction was lyophilized.

EXAMPLE 12

2-(4'-carboxyphenylazo)-6-acetylmorphine-BSA

To a solution of 500 mg bovine serum albumin (BSA) in 20 ml distilled water was added a solution of 75 mg 2-(4'-carboxyphenylazo)-6-acetylmorphine in 5 ml of 0.01 M NaOH and the pH of the resulting solution was adjusted to 3.9–4.1 with 1 N HCL. To this solution was added 80 mg of 1-cyclohexyl-3-(2-morpholinoethyl) carbodiimide metho-p-toluene sulfonate and the reaction mixture was stirred for 6 hours at 4° C while monitoring the pH. The pH was adjusted to 7.0 and the unreacted 2-(4'-carboxyphenylazo)-6-acetylmorphine was separated from the protein conjugate by passage down a G-25 Sephadex column using distilled water as the eluant. The protein fraction was collected and concentration determined by optical density measurement and then diluted to a 1% solution by addition of distilled water.

The procedure for coupling to keyholelimpet hemocyanin is identical.

Although aqueous media were employed in the foregoing examples of coupling reactions, other suitable solvent media can be employed. Exemplary are salt solutions, generally ranging from about 0.10 to about 0.20M salt solution (NaCl) or buffered salt solutions using, for example, a phosphate buffer (0.01–0.05M, pH7–7.5). The foregoing salt solutions can also be buffered with similar phosphate buffering agents. Solvents which react with or denature proteins should generally be avoided. Examples are organic solvents, such as alcohols, ethers and the like, or strong inorganic acids or bases, as for example, mineral acids, or alkali hydroxides. When other non-protein carrier materials are employed, the above restrictions do not apply and a wide variety of organic solvents can be employed so long as they are inert under the reaction conditions utilized in carrying out the coupling reaction.

Antigens of structure (1) may be prepared by conjugation to immunogenic carriers in the foregoing fashion, with compounds of formula R—N=Y—R'—A, where R, Y, R', and A are as previously defined, A being a functional group capable of reacting with functions of Z to form the linkage L. The compound of formula (1) can be obtained by effecting keto-amino condensation of an aromatic aldehyde having a function A other than the keto group with a Z-amino-3-oxybenzomorphan. For example, to an ethanolic solution containing 3 g. of 2-aminomorphine, may be added an ethanoiic solution containing 1.5 g. of 4-carboxybenzaldehyde. The reaction mixture is then refluxed for 4 hours, cooled, and concentrated in volume for separation of N-(4'-carboxyphenylidene)-2-aminomorphine, as by column chromatography. The 2-aminomorphine and 2-amino derivatives of other 3-oxybenzomorphans (e.g., heroin, monoacetyl morphine, etc.) can be secured by reduction of the 2-(4'-carboxyphenylazo)-3-oxybenzomorphans otherwise employed for conjugation to form antigens of formula (1) in the preferred embodiments of the invention.

According to a somewhat different embodiment of the invention, one may prepare immunogenic carrier conjugates (conjugated as before) of the hapten 1-acetomorphine [L. Small and J. E. Mallonee, *J. Org. Chem.*, 12:558 (1947)]. Thus, keto-amino condensation of 1-acetomorphine and a primary aromatic amine $R'—NH_2$ having a function other than the primary amino group capable of reaction with carrier Z to form the linkage L (e.g., p-aminobenzoic acid) at reflux temperature, e.g.:

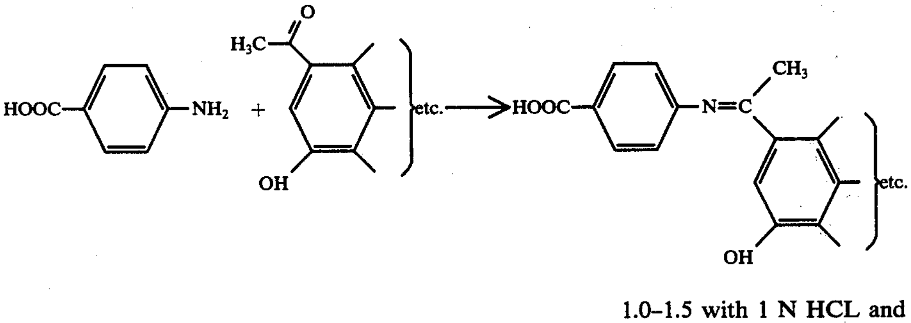

An alternative method of forming synethtic antigens according to this invention is next illustrated.

Reaction Sequence II

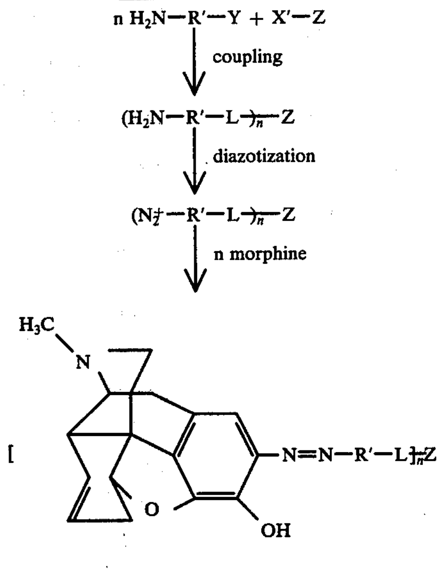

In this reaction sequence R' is the aromatic component of a primary aromatic amine as previously defined, and Y is that substituent on R' capable of reacting with a functional group X' of Z, the immunogenic carrier, to form a linking moiety L. Preferably in the case of Reaction Sequence II,Y is —COOH, $—CH_2COOH$ or $—CH_2CH_2COOH$. Z is as previously defined. Coupling of functional group Y to immunogenic carrier Z is conventionally effected, as by the carbodiimide condensation previously described. Coupling of the conventionally formed diazonium salt to 3-oxybenzomorphan, such as morphine, provides the "reverse-coupled" antigen. The following example illustrates the reverse coupling procedure as it may be applied to morphine-polylysine conjugation.

EXAMPLE 13

Reverse Coupling

A. Diazotized Polylysine-PABA

A solution of 100 mg polylysine-para-aminobenzoic acid (PABA) in 5 ml of distilled water is adjusted to pH 1.0–1.5 with 1 N HCL and cooled to 0°–5° C. A cold solution of 100 mg sodium nitrite in 0.5 ml of distilled water is added to an end point with potassium iodide starch paper. The solution is stirred at 0°–5° C for 30 minutes and excess nitrous acid decomposed with sulfamic acid as monitored with potassium iodide starch paper.

B. Coupling of diazotized polylysine-PABA to morphine

The 100 mg of polylysine-PABA diazotized as above is added to a 0°–5° C solution of 300 mg of morphine sulfate in 10 ml distilled water previously adjusted to pH 10.5 with 6N NaOH. (The pH is maintained around 10.5 during the addition with 1N NaOH). The reaction mixture is stirred overnight (9 hours) in the cold, the pH being maintained at 10–10.5 for the first hour with 1 N NaOH. The conjugate is dialyzed against 6 liters of 0.1 M sodium carbonate for 10 days with twice daily changes of the distilled water. The solution of conjugate is lyophilized to yield 130 mg of polylysine-morphine conjugate.

EXAMPLE 14

The procedure of Example 1, including portions A and B, is repeated employing an equivalent amount of 3-methoxy-N-methylmorphinan sulfate monohydrate in place of the morphine sulfate monohydrate with equivalent results.

EXAMPLE 15

The procedure of Example 5 is repeated employing an equivalent amount of the product of Example 14 in place of the 2-(4'-carboxyphenylazo)morphine with equivalent results.

EXAMPLE 16

The procedure of Example 1 is repeated employing an equivalent amount of levophenacylmorphan sulfate monohydrate in place of the morphine sulfate monohydrate with equivalent results.

EXAMPLE 17

The procedure of Example 5 is repeated employing the product of Example 16 with equivalent results.

The synthetic antigens of this invention are typically prepared for the purpose of raising antibodies which are specific to the native, unaltered 3-oxybenzomorphan haptens, and this is the usual case. However, it is well recognized that these native haptens are converted, in vivo, in the body to metabolic products including glucuronide esters. Therefore, instead of assaying for the native, unaltered haptens, it may be desirable to actually assay for these metabolites. Synthetic antigens to these derivatives can be prepared by coupling the glucuronide metabolites, as by carbodiimide condensation, to immunogenic carriers. In such cases, coupling occurs through the carboxylic group of the glucuronic acid to form a linking group with the reactive functional group of the immunogenic carrier. In the case of immunogenic protein carrier, an amide linkage is formed. The following illustrates the preparation of such a synthetic antigen.

EXAMPLE 18

Morphine-3-yl-B-D-glucopyranosiduronic Acid-Bovine serum albumin (Morphine glucuronide-BSA)

To a solution of 500 mg bovine serum albumin in 20 ml distilled water is added a solution of 100 mg morphine-3-yl-$\beta$-D-glucopyranosiduronic acid in 5 ml 0.01M sodium hydroxide and the pH of the resulting solution is adjusted to 3.9 to 4.1 with 1 N hydrochloric acid. To this solution is added 100 mg of 1-cyclohexyl-3-(2-morpholino-ethyl) carbodiimide metho-p-toluene sulfonate and the reaction mixture is stirred for 12 hours at 4° C while monitoring the pH. The pH is adjusted to 7.0 and the solution dialyzed against 6 liters of 0.15 M sodium carbonate at 4° C for 1 week with daily changes of sodium carbonate solution. It is next dialyzed against 6 liters of 0.1M sodium phosphate buffer (pH 7.4) at 4° C for 2 days with daily changes of the phosphate buffer solution. The protein concentration is determined by measurement of optical density and adjusted to a 1% solution with distilled water.

Antisera to conjugate produced according to this invention are raised by conventional procedures. Table 4 below indicates administration and bleeding schedules for both intravenous (IV) and multiple subcutaneous site (MSQ) administration procedures, variously for goat and rabbit hosts. All subcutaneous injections are made with 50:50 volume mixtures, Freund's adjuvant to aqueous conjugate solution containing the stated amount of conjugate. For rabbits, total "dose" per administration is about 1 ml. in the case of subcutaneous injection (about ¼ ml. per site), and about ¼ ml. aqueous solution in the case of intravenous administration. In the case of goats, total "dose" per administration is 2 ml. in the case of subcutaneous injection (about ½ ml. per site); and ½ ml. aqueous solution in the case of intravenous administration. Each goat bleeding is of 300–400 ml., yielding about 125 ml. serum. Each rabbit bleeding is of 40–50 ml., yielding about 20–25 ml. serum. Each crude antiserum sample may be monitored by RIA or by ring tests with conjugates to heterologous protein to ascertain the presence of antibody. In the case of the intravenous course, 600 mg. boosters are administered each 4th week following week 14, with further bleeding 7–10 days after each booster. Following week 15 of the MSQ course 2 mg. (rabbit) and 4 mg. (goat) boosters are administered each 4th week after week 15, with bleeding 3 weeks after each booster.

Table No. 4

| Week No. | 1 | 2 | 3 | 4 | 5 | 6 | 7 | 8 |
|---|---|---|---|---|---|---|---|---|
| MSQ (Rabbit) | 1 mg MSQ | — | — | Bleed, 5 mg MSQ | — | — | Bleed, 2 mg MSQ | — |
| MSQ (Goat) | 2 mg MSQ | — | — | Bleed, 10 mg MSQ | — | — | Bleed, 4 mg MSQ | — |
| IV (Rabbit) | 6 mg MSQ | — | — | Bleed, 3.5 mg IV | — | Bleed, 600 mg IV | — | Bleed |
| IV (Goat) | 12 mg MSQ | — | — | Bleed, 7 mg IV | — | Bleed, 600 mg IV | — | — Bleed |

| Week No. | 9 | 10 | 11 | 12 | 13 | 14 | 15 |
|---|---|---|---|---|---|---|---|
| MSQ (Rabbit) | Bleed, 2 mg MSQ | — | 2 mg MSQ | — | Bleed | — | 2 mg MSQ |
| MSQ (Goat) | Bleed, 4 mg MSQ | — | 4 mg MSQ | — | Bleed | — | 4 mg MSQ |
| IV (Rabbit) | — | 600 mg IV | — | Bleed | — | 600 mg IV | — |
| IV (Goat) | — | 600 mg | — | Bleed | — | 600 mg | — |

Table No. 4-continued

| IV | IV |
|---|---|

Crude IgG may be extracted from serum shown positive by ring testing by passage through DEAE Sephadex A-50, and may thereafter be refined as by the immunoadsorption techniques generally described in my aforesaid application Ser. No. 89,929. In the following Example, those techniques are employed to obtain essentially pure antibody raised to "azomorphine".

EXAMPLE 19

Antibody Purification

The aryl-pendant amino groups of para-aminobenzyl cellulose were diazotized and coupled to morphine essentially as in the conjugation step of Example 1, supra. The dried sorbent (300 mg) was washed with 50 ml. saline (0.9%) five times and suspended in a final volume of 15 ml, to which 5 ml of crude antiserum raised to the azomorphine conjugate of Example 5, supra was added. After stirring at 4° C for 10 hours, the morphine-sorbent was washed exhaustively with saline, then with distilled water. The matrix recovered by centrifugation was used as a slurry. 10 ml, 15M HCL was added to sorbent. After centrifugation for 1 minute the filtered supernatant was neutralized at once with 1 M dibasic sodium phosphate. The acid base cycle was repeated three times. The recovered antibody solution was dialyzed against 12 liters of 0.1 M phosphate buffer, pH 7.4. Yields were 250–1200 mg antibody IgG/ml. Uncontaminated IgG was demonstrated by immunoelectrophoresis. UV absorbance confirmed the absence of unbound hapten derivative. The specificities of recovered antibody IgG were next determined by immune fluorescence techniques.

EXAMPLE 20

Fluorescence Quenching

The morphine specificity of antibody IgG prepared in Example 5, supra and purified by immunoadsorption as just described was demonstrated by antibody fluorescence inhibition testing, in which 2-(4'-carboxyphenylazo) morphine ("azomorphine"), which quenches antibody fluorescence upon binding, is made to compete for binding sites with morphine and, for comparative purposes, other native alkaloids (codeine, monoacetyl morphine, heroin and dextromethorphan).

Quenching of antibody fluorescence was performed using antibody IgG from non pooled samples. Quenching maxima were 56–77%. Association constants determined by the Sips equation applied to fluorescence data ranged from $1 \times 10^7$ to $3 \times 10^8$ liters/mole. Native alkaloid was added in increasing amounts to each tube containing azomorphine and IgG in a 10:1 hapten: antibody ratio ($\times 10^{-10}$ moles/ml). The alkaloid was added to IgG simultaneously with or in advance of azomorphine. All dilutions were done in triplicate. Incubations including controls were carried out for 10 minutes to 12 hours at 23° C. Typically, homologous native morphine at a concentration of $40 \times 10^{-10}$ moles/ml completely inhibited fluorescence quenching of $1 \times 10^{-10}$ moles/ml antibody by $10 \times 10^{-10}$ moles/ml azomorphine. Inhibition by native codeine, monoacetyl morphine (C-3 hydroxyl free) heroin and dextromethorphan was slight even in vast hapten excess as is apparent from FIG. 1 of the drawing, in which resulting data are graphically presented, the purified antibody failed to "recognize" the morphine surrogates.

EXAMPLE 21

Radioimmune Assay for Cross-Reactivity

Radioimmune assay was performed by incubating various dilutions of crude antisera (obtained by bleeding animals challenged with the morphine conjugate of Example 5) with tritiated 7,8-dihydro-morphine (New England Nuclear Corp., 715 mC/mM, 8 picomoles, 3500 cmp) in the presence of normal male human plasma at 4° C, pH 7.6–7.6. After 2 hours, an equal volume of a neutral, saturated ammonium sulfate solution was added. The resulting precipitates, sedimented by centrifugation at 3000 rpm for 15 minutes at 4° C, were washed once in 50% saturated ammonium sulphate solution. Each precipitate was dissolved in 0.2 ml NCS solubilizer (Amersham-Searle Corp.) and transferred to a scintillation counting vial containing 10 ml. Aquasol dispersant (New England Nuclear Corp.) and counted in a Nuclear Chicago Liquid Scintillation Spectrometer. The addition of increasing amounts of unlabeled morphine to a fixed amount of dihydromorphine —$H^3$ and antiserum resulted in competitive inhibition of the labeled dihydromorphine bound to the antibody. The relationship of the amount of unlabeled morphine added to inhibition of binding was as follows:

TABLE 5

| Nanograms of Unlabeled Morphine Added | % Inhibition of Dihydromorphine $H^3$ Binding |
|---|---|
| 0.5 | 40 |
| 0.75 | 51 |
| 1.0 | 59 |
| 2.0 | 77 |
| 10.0 | 95 |

Additional data is graphically presented in FIG. 2 of the drawing. Cross-reactivity of the antiserum with other opium alkaloids and analogs is tabulated below. Cross-reactivity was computed by the method of Abraham, *J. Clin. Endocrin. & Metab.* 29, 866,1969 with morphine taken as 100%. The amount ($M_{50}$) of morphine (ng) required to inhibit antibody binding of the labeled hapten (tritiated dihydromorphine) by 50% was divided by the amount ($A_{50}$) of the compound assayed for cross-reactivity which is required to inhibit binding of the labeled hapten by 50%. Cross-reactivity data obtained in this experiment is reported in Table 6.

TABLE 6

| Cross-reactivity of Antibody Raised to Azomorphine Conjugate | |
|---|---|
| Alkaloid | % Cross-reactivity |
| Morphine | 100 |
| Codeine | 11 |
| Ethylmorphine | 16 |
| Methadone | 0.01 |
| Dextromethorphan | 0.01 |
| Diacetylmorphine | 7 |
| Monoacetylmorphine | 7 |
| N-allylnormorphine | 2 |

More generally, the invention can be said to provide immunoglobulin compositions comprising an immunoassay-effective amount of antibody specific to morphine, which antibody cross-reacts not more than on the order of about 0.1% with methadone and dextromethorphan, and not more than about 10% with mono- and diacetylmorphine under the conditions just described. Similarly measured, cross-reactivity of antibody taken as 100% reactive with morphine is on the order of about 100% with the azomorphine derivative to whose immunogenic conjugate the antibody is raised [in the case of Example 21, 2-(4'-carboxyphenylazo morphine)]. Further, cross-reactivity of the morphine-specific antibody with codeine does not exceed 20%.

I claim:

1. An antigen of formula:

$[R—N=Y—R'—L]_n Z$, where R is a 3-oxybenzomorphan compound; Y is selected from the class consisting of N and CH and is connected to a ring carbon atom of an aromatic component of R', R' also having a moiety capable of reacting with a functional group of Z; Z is a carrier molecule conferring immunogenicity, the combination of the moiety of R' and the functional group of Z forming the linking group L; and *n* is from 1 to the number of available functional groups on Z in its conjugated state; when Y is N, a diazo linkage is present, this diazo linkage being formed by diazotization of a primary amino group on the material from which R' formed; when Y is CH, R' is the remaining aromatic component of an aromatic aldehyde, and CH is the condensation residue of the characteristic keto group of the aldehyde, where bonding to R is through an available ring carbon atom of the aromatic ring of the 3-oxybenzomorphan hapten moiety.

2. An antigen according to claim 1 wherein R is selected from the group consisting of 2-morphinyl, 2-monoacetylmorphinyl and 2-(3,6-diacetylmorphinyl).

3. An antigen according to claim 2 wherein Z is an immunogenic carrier protein and wherein Y is =N—.

4. An antigen according to claim 2 of structure

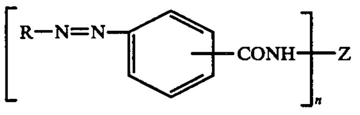

5. An antigen according to claim 2 of structure

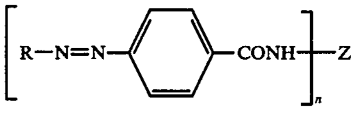

6. An antigen according to claim 1 wherein Z is selected from the group consisting of bovine serum albumin, keyhole limpet hemocyanin and thyroglobulin.

7. An antigen according to claim 3 of structure

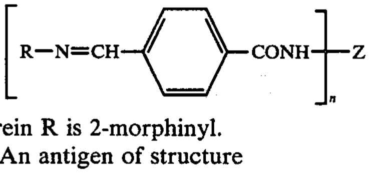

wherein R is 2-morphinyl.

8. An antigen of structure

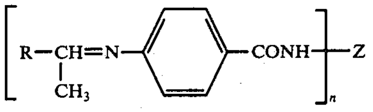

where bonding to R is through an available ring carbon atom of the aromatic ring of the 3-oxybenzomorphan hapten moiety.

9. The antigen of claim 1 wherein R is a 3-oxymorphan glucuronide.

10. The material of claim 3 wherein R is 3-morphin-3-yl-β-D-glucopyranosiduronic acid.

11. An antigen according to claim 1 wherein Z is an immunogenic carrier protein and wherein Y is CH.

12. The antigen of claim 1 wherein R is a member selected from the class consisting of 3-methoxy-N-methyl morphinan, N-cyclopropylmethyl morphinan, N-β-furylethyl levorphanol, N-p-aminophenethyl levorphanol, levophenacylmorphan.

13. Antibody raised by the antigen of claim 1 and specific to the hapten of said antigen.

14. Antibody raised by the antigen of claim 2 and specific to the hapten of said antigen.

15. Antibody raised by the antigen of claim 3 and specific to the hapten of said antigen.

16. Antibody raised by the antigen of claim 10 and specific to the hapten of said antigen.

17. An immunochemical method of assaying for the presence of a 3-oxybenzomorphan target in a sample, wherein said method employs an antibody obtained by the immunologic response of a vertebrate animal to administration of an antigen according to claim 1 and wherein said said antibody is specific to the target, said method also employing a standard, the antibody binding with the target to form an antibody-target complex and competitively binding with the standard to form an antibody-standard complex, the antibody-standard complex having an artificially introduced radiation label enabling the complex to be assayed quantitatively by measurement of radiation emanating from it, the affinities of the antibody for the standard and for the target being known quantitatively, said method comprising allowing a known quantity of the sample and a known quantity of the standard to compete for binding with a known quantity of the antibody and determining the radiation emanating from the antibody-standard complex, thereby enabling the quantity of antibody-bound standard to be calculated and the quantity of target in the sample to be deduced.

18. The method of claim 17 wherein the label is radioactive and the antibody-standard complex is separated from any non-complexed labeled material after allowing competition binding and before determination of the emanated radiation.

19. The method of claim 17 wherein the label is fluorescent and the standard is provided with a chemical moiety giving it a fluorescence spectrum overlapping the natural fluorescence spectrum of the antibody, whereby the complex can be assayed by measurement of the perturbation of the antibody fluorescence due to its binding with the standard.

20. An immunochemical method of assaying for the presence of a 3-oxybenzomorphan metabolite target in a sample, wherein said method employs an antibody obtained by the immunologic response of a vertebrate animal to administration of an antigen according to claim 1 and wherein said antibody is specific to the target, said method also employing a standard, the antibody binding with the target to form an antibody-target complex and competitively binding with the standard to form an antibody-standard complex, the antibody-standard complex having an artificially introduced radiation label enabling the complex to be assayed quantitatively by measurement of radiation emanating from it, the affinities of the antibody for the standard and for target being known quantitatively, said method comprising allowing a known quantity of the sample and a known quantity of the standard to compete for binding with a known quantity of the antibody and determining the radiation emanating from the antibody-standard complex, thereby enabling the quantity of antibody-bound standard to be calculated and the quantity of target in the sample to be deduced.

21. The method of claim 20 wherein the label is radioactive and the antibody-standard complex is separated from any non-complexed labeled material after allowing competition binding and before determination of the emanated radiation.

22. The method of claim 20 wherein the label is fluorescent and the standard is provided with a chemical moiety giving it a fluorescence spectrum overlapping the natural fluorescence spectrum of the antibody, whereby the complex can be assayed by measurement of the perturbation of the antibody fluorescence due to its binding with the standard.

23. An immunoglobulin composition comprising an immunoassay-effective amount of antibody specific to a 3-oxybenzomorphan compound, said antibody being raised by an antigen according to claim 1, said antibody cross-reacting not more than on the order of about 0.1% with methadone and dextromethorphan, as determined by radioimmune inhibition assay employing 7,8-tritiated dihydromorphine as the labeled hapten, percent cross-reactivity being determined according to the equation $$\frac{M_{50}}{A_{50}} \times 100$$

wherein $M_{50}$ is the amount of morphine required to inhibit antibody binding of said labeled hapten by 50% and $A_{50}$ is the amount of the compound assayed for cross-reactivity which is required to inhibit binding of said labeled hapten by 50%.

24. A composition according to claim 23 wherein said antibody so cross-reacts not more than on the order of about 10% with monoacetylmorphine and diacetylmorphine when said monoacetylmorphine and diacetylmorphine are incubated with said composition and tritiated dihydromorphine for 2 hours at about pH 7.6–7.7 and 4° C.

25. A composition according to claim 23 wherein said antibody so cross-reacts at least about 100% with 2-(4'-carboxyphenylazo) morphine.

26. A composition according to claim 23 wherein said antibody so cross-reacts not more than about 20% with codeine.

* * * * *